United States Patent [19]

Heckele

[11] 4,265,561
[45] May 5, 1981

[54] HOLDERS FOR MEDICAL APPARATUS

[75] Inventor: Helmut Heckele, Knittlingen, Fed. Rep. of Germany

[73] Assignee: Richard Wolf GmbH, Knittlingen, Fed. Rep. of Germany

[21] Appl. No.: 63,035

[22] Filed: Aug. 2, 1979

[30] Foreign Application Priority Data

Aug. 16, 1978 [DE] Fed. Rep. of Germany ... 7824396[U]

[51] Int. Cl.³ .......................... F16B 2/10; A61B 1/00; A61B 10/00
[52] U.S. Cl. ......................................... 403/3; 403/90; 403/115; 128/4; 128/21; 128/23; 362/105
[58] Field of Search ...................... 403/3, 90, 115, 56, 403/131, 122, 59; 2/452, 171, 171.2, DIG. 11; 128/21, 22, 23, 4; 248/285, 286; 362/105, 106

[56] References Cited

U.S. PATENT DOCUMENTS

| 169,383 | 11/1875 | Starr | 403/90 |
| 428,761 | 5/1890 | Sardy | 2/452 X |
| 1,538,191 | 5/1925 | Lando | 128/21 X |
| 1,688,113 | 10/1928 | Bornkessez | 128/23 |
| 1,695,009 | 12/1928 | Cochran | 403/90 X |
| 1,703,704 | 2/1929 | Anzell | 403/90 X |
| 3,072,426 | 1/1963 | Gilbert | 403/115 |
| 3,212,740 | 10/1965 | Greenberg | 403/90 X |
| 3,830,230 | 8/1974 | Chester | 362/105 X |
| 3,957,241 | 5/1976 | Morris et al. | 403/90 X |

OTHER PUBLICATIONS

Head Bands, The George P. Pilling & Son Co. Philadelphia-1921, p. 292.

Primary Examiner—James Kee Chi
Attorney, Agent, or Firm—Kinzer, Plyer, Dorn & McEachran

[57] ABSTRACT

A head band has two ball and socket joints spaced apart by a distance approximately equal to the human interocular distance, said joints including balls each of which is bored non-circularly to receive a retaining rod arranged to be passed selectively through and axially adjustable in the bore in one of said balls, said retaining rod being provided with a clamping device at its free end for receiving and clamping an endoscope.

4 Claims, 1 Drawing Figure

U.S. Patent      May 5, 1981      4,265,561
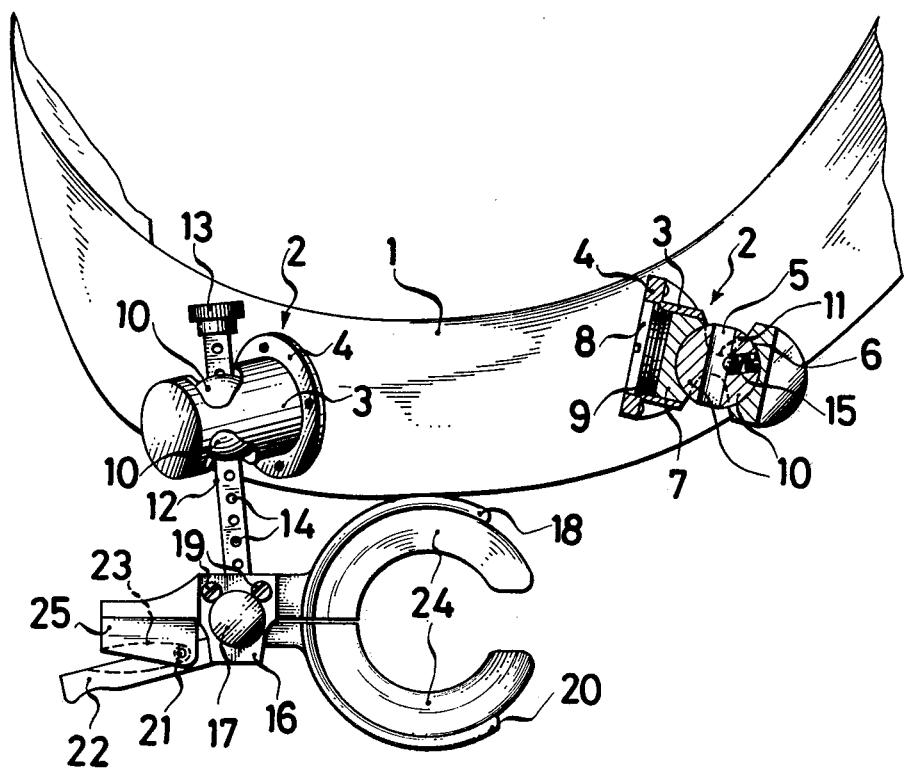

HOLDERS FOR MEDICAL APPARATUS

BACKGROUND OF THE INVENTION

The present invention relates to holders for medical apparatus of the kind comprising a head band provided with a ball and socket joint to receive a ball provided with a carrier and which can move slightly in all directions but is held under friction.

It is known to mount head bands with bearing blocks for holders of medical apparatus such as lamps, endoscope or similar articles, a ball connected with a carrier being resiliently mounted in a ball socket in a cylindrical bearing block, said ball being capable of limited movement in all directions but which can be locked in an adjusted position in the socket by friction.

It is an object of the invention to provide a head band such that an endoscope can be securely and replaceably supported with the ball and socket joint in such a manner that its eyepiece can be placed as desired close to either the left or right eye of the doctor.

SUMMARY OF THE INVENTION

Accordingly, in a holder of the kind hereinabove described the invention consists in that said head band has two ball and socket joints spaced apart by a distance approximately equal to the human interocular distance, said joints including balls each of which is bored noncircularly to receive a retaining rod arranged to be passed selectively through and axially adjustable in the bore in one of said balls said retaining rod being provided with a clamping device at its free end for receiving and clamping an endoscope.

It is thus possible to insert the retaining rod with the clamping device for the endoscope into the ball section of one or other ball and socket joint of the head band according to whether the doctor wishes to use his left or his right eye and to so adjust the projected length of the rod as well as angular position to any of its limited positions whereby the eye piece of the endoscope which is to be clamped on may directly face the doctor's selected eye.

BRIEF DESCRIPTION OF THE DRAWINGS

In order that the invention may be more clearly understood, reference will now be made to the accompanying drawing which somewhat schematically, shows one embodiment thereof by way of example.

DETAILED DESCRIPTION OF THE PREFERRED EMBODIMENT

Referring to the drawing, a head band 1 is provided with two bearing blocks 2 for the two ball and socket which are spaced apart by a distance approximately equal to the human interocular distance. These bearing blocks 2 each consist of a cylinder 3 which is mounted to project vertically away from the head band 1 by means of a flange 4. Each cylinder 3 is provided with a transverse bore 5 extending from top to bottom in two the position shown and defining a ball socket at each end. The outer ball socket is shown at 6, and the inner ball socket is shown at 7, this latter being spring-loaded by means of a compression spring 9 bearing on a base 8 which is screwed into the socket or cup 7 to face the outer ball socket or cup 6. The two ball sockets 6, 7 have a ball 10 between them which is provided with a non-circular bore 11 which may be for example of square cross section, in the area of the bore 5.

A retaining rod 12 with a suitable cross section is selectively passed through the ball bore 11 of one or other bearing block 2 after loosening of a screw head 13. The rod 12 is provided with notches 14 along its length in which a small, radially sprung, stop ball 15 mounted in the ball and socket joint 10 catches and which fixes the retaining rod 12, the projecting length of which can be varied, in its adjusted position.

The free end of the supporting rod 12 catches in a square bore of a bearing block 16 which is mounted by a means of a knurled-head screw 17 on the retaining rod 12. One jaw 18 of a clamping device for an endoscope, (which is not shown), is rigidly connected to the bearing block 16 by means of screws 19. The other jaw 20 is pivotably mounted at 21 to the block 16 and is provided with an opposed lever arm 22 which is forced apart by a spring 23 for closing the jaws 18, 20. The jaws 18, 20 are lined with a plastics material 24 so as to support the endoscope without damaging it. The lever arm 22 is furthermore kept from tilting on either side by a sheet metal channel member 25.

The retaining rod 12 alternatively may be articulatedly connected to the bearing block 16 and the joint can be secured, or the retaining rod 12 may be sub-divided by a lockable joint.

For utilisation, the endoscope is inserted by opening the jaws 18, 20 by activating the lever arm 22 against the spring 23 and is held firm on release of the lever arm 22. Now the doctor, by swiveling the retaining rod 12 with the ball and socket joint which can be held by friction and by adjusting the projection length of the retaining rod by the ball and socket joint 10, can so adjust the endoscope that the eye piece is near the eye so that the doctor has both hands free for other operations. According to whether he is left or right eyed the retaining rod can be connected with one of the other ball and socket joint 2.

I claim:

1. In a holder for medical apparatus of the kind comprising a head band provided with a ball and socket joint to receive a ball provided with a carrier and which can move slightly in all directions but is held under friction, the improvement which consists in that said head band has two ball socket joints spaced circumferentially apart thereon by a distance approximately equal to the human interocular distance, said joints including rigidly supported sockets in which are swivelled balls each of which in turn is bored non-circularly to receive a retaining rod arranged to be passed selectively through and axially adjustable in the bore in one of said balls, said retaining rod being provided with a clamping device at its free end for receiving and clamping an endoscope, whereby the surgeon may support the endoscope at the better eye and may raise or lower the rod and swivel it to adjust the endoscope for elevation and range in front of the better eye.

2. A holder according to claim 1, wherein each ball and socket joint consists of a cylinder attached to the band so as to project outwardly from said head band and being transversely bored to define inner and outer ball socket means, the inner one of said ball socket means being spring-loaded whereby said two ball socket means can hold and grip said bored ball by friction.

3. A holder according to claim 1 or 2, wherein said retaining rod is notched along its length to receive a spring-loaded stop ball provided within each said ball and socket joint in the manner of a catch.

4. A holder according to claim 3, wherein said clamping device comprises a bearing block mounted on one end of said retaining rod to which block one of a pair of clamping jaws is rigidly connected, the other said clamping jaw being pivotally mounted on said bearing block against spring pressure.

* * * * *